(12) United States Patent
Everland et al.

(10) Patent No.: US 10,123,908 B2
(45) Date of Patent: Nov. 13, 2018

(54) METHOD OF PREPARING A WOUND CARE DEVICE

(75) Inventors: Hanne Everland, Bagsværd (DK); Kurt Osther, Scottsdale, AR (US); Jacob Vange, Helsingør (DK); Lene Feldskov Nielsen, Copenhagen (DK)

(73) Assignee: Coloplast A/S, Humlebaek (DK)

( * ) Notice: Subject to any disclaimer, the term of this patent is extended or adjusted under 35 U.S.C. 154(b) by 454 days.

(21) Appl. No.: 14/125,586

(22) PCT Filed: Jul. 10, 2012

(86) PCT No.: PCT/DK2012/050264
§ 371 (c)(1),
(2), (4) Date: May 21, 2014

(87) PCT Pub. No.: WO2013/007266
PCT Pub. Date: Jan. 17, 2013

(65) Prior Publication Data
US 2014/0248420 A1  Sep. 4, 2014

(30) Foreign Application Priority Data

Jul. 10, 2011 (DK) .................................. 2011 00525

(51) Int. Cl.
*A61F 13/00* (2006.01)
*A61L 15/26* (2006.01)
*A61L 15/38* (2006.01)
*A61L 15/32* (2006.01)
*A61L 15/42* (2006.01)

(52) U.S. Cl.
CPC ........ *A61F 13/00991* (2013.01); *A61L 15/26* (2013.01); *A61L 15/32* (2013.01); *A61L 15/38* (2013.01); *A61L 15/425* (2013.01); *A61L 2400/04* (2013.01)

(58) Field of Classification Search
CPC ..... A61F 13/16; A61F 13/00; A61F 13/00991
USPC ............................................ 604/369; 602/52
See application file for complete search history.

(56) References Cited

U.S. PATENT DOCUMENTS

| 4,664,662 | A | * | 5/1987 | Webster ............ A61F 13/00021 602/47 |
| 6,350,609 | B1 | | 2/2002 | Morozov |
| 2005/0038369 | A1 | * | 2/2005 | Gregory ............ A61F 13/00012 602/48 |

(Continued)

FOREIGN PATENT DOCUMENTS

| CN | 1984688 | 3/2008 |
| GB | 221209 | 7/1992 |

(Continued)

OTHER PUBLICATIONS

Family Overview of CN1984688.

*Primary Examiner* — Dah-Wei D Yuan
*Assistant Examiner* — Andrew Bowman
(74) *Attorney, Agent, or Firm* — Coloplast Corp., Coloplast A/S; Nick Baumann

(57) ABSTRACT

The present invention relates to method of preparing an absorbent wound care device comprising an active agent on a wound contacting surface, such as e.g. a protein or an enzyme, by the use of electrospraying, and a wound care device obtained by said method. The invention further relates to a wound care device comprising Thrombin and a polyurethane foam, and a method of treating bleeding.

6 Claims, 8 Drawing Sheets

(56) References Cited

U.S. PATENT DOCUMENTS

| | | | |
|---|---|---|---|
| 2006/0014030 A1* | 1/2006 | Langen | A61F 13/00008 |
| | | | 428/447 |
| 2007/0225631 A1* | 9/2007 | Bowlin | A61K 38/363 |
| | | | 602/52 |
| 2008/0064999 A1 | 3/2008 | Larsen et al. | |
| 2010/0172958 A1 | 7/2010 | Lucchesi et al. | |
| 2011/0294911 A1* | 12/2011 | Schoberger | A61L 15/26 |
| | | | 521/70 |

FOREIGN PATENT DOCUMENTS

| | | |
|---|---|---|
| GB | 2268907 | 1/1994 |
| WO | 2005035010 | 4/2005 |
| WO | 2006007844 | 1/2006 |
| WO | 2009126870 | 10/2009 |

* cited by examiner

| C | Control | | Patch with thrombin (30 U/cm$^2$) | |
|---|---|---|---|---|
| T = 0 |  | No haemostatic effect. Patch is pushed away from wound by the blood |  | Haemostatic effect of patch. No blood in the center of the patch. Blood on the patch is from the surroundings |
| T = 1 |  | Wound is bleeding beneath the patch |  | Haemostatic effect |
| T = 5 |  | Wound is bleeding beneath the patch |  | Haemostatic effect |

METHOD OF PREPARING A WOUND CARE DEVICE

FIELD OF THE INVENTION

The present invention relates to a method of preparing an absorbent wound care device comprising an active agent by the use of electrospraying, and a wound care device obtained by said method. The invention further relates to a wound care device comprising thrombin and a polyurethane foam, and a method of treating bleeding.

BACKGROUND

Applying an amount (often a small amount) of active agent onto a restricted area of an absorbent device may be difficult. In British patent application nos. GB 2 268 907 and GB 2 251 209, a method of printing on foam is disclosed. The print is deposited on a carrier and then transferred from the carrier to the foam by the application of heat and pressure. The method is laborious and not suitable for sensitive compositions, as they may suffer from the heat and pressure treatment by, e.g., degradation.

WO 06007844 describes a wound care device, wherein an active agent is applied to an absorbent element by spray coating.

SUMMARY

The inventors herein describe a new method of applying an active agent onto a surface. It is shown that by electrospraying an active agent onto a surface, an exact pattern and amount can be deposited. Utilizing the electrospraying technique, the activity of, e.g., enzymatically active agents is maintained.

DETAILED DISCLOSURE

Figure 1:
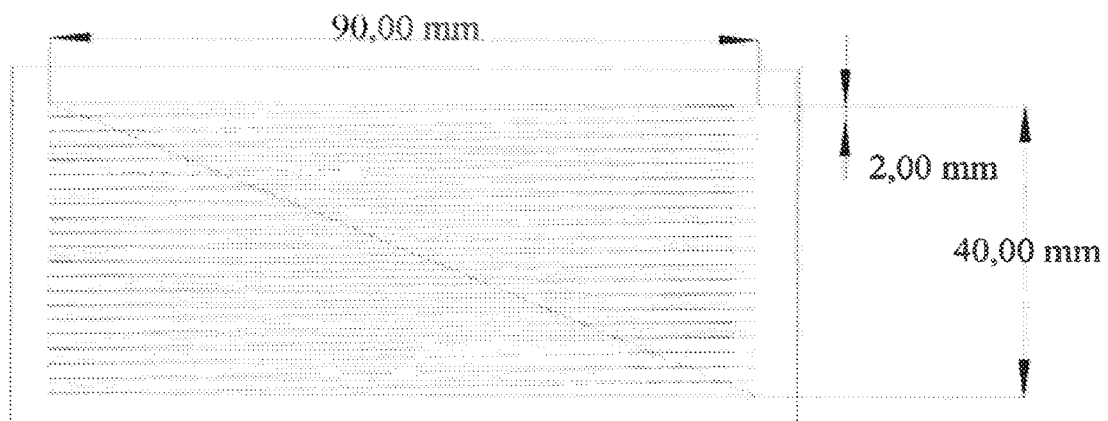
FIG. 1: Example of Pattern structure for electrospraying.

A first aspect of the present invention relates to a method of preparing an absorbent wound care device comprising the steps of:
a) providing a wound care device comprising an absorbent element, said element having a wound contacting surface and opposite thereof a backing surface;
b) providing an active agent, and
c) applying the active agent by electrospraying to the wound contacting surface of the absorbent element.

This method provides for minimal waste during the process. That is, all of the active agent leaving the nozzle is placed on the absorbent surface. Not only is it a very efficient use of active agent—some of which are very expensive. It also minimizes the health risks when working with active agents, as none is spread to the surroundings during the process.

The present method further allows for accurate dosing of the active agent. This is particularly important for highly potent agents where only small amounts are necessary for achieving the desired effect and, for example, in cases where small derivations from the intended dosage may even cause undesirable adverse effects. Additionally, by applying electrospraying, the active agent will be evenly distributed in a controllable manner.

In one embodiment of the method according to the invention, the electrospraying step comprises:
i) having a stationary charged spray nozzle with the active agent, and
ii) having an opposing stationary neutral unit, wherein the wound contacting surface of the absorbent element is moving in-between the spray nozzle and the neutral unit. This configuration minimizes the vibrations caused by moving the absorbent surface such that a stable jet from the spray nozzle is formed. Hereby, the accuracy of the process is increased and waste of materials is even further limited.

In a preferred embodiment of the invention, the spray nozzle is negatively charged.

Depending on the nature of the active agent, it may particularly be preferred that the active agent is in an aqueous solution. However, aqueous emulsions may alternatively be preferred.

The phrase "wound contacting surface of the absorbent element", as used herein, is intended to mean an outer surface of the absorbent element, being the surface in direct contact with a wound when the wound care device is in use. Additionally, the term "surface" of an absorbent element is intended to mean an outer surface, as opposed to the interior of the absorbent element. Accordingly, when a thin layer of active agent is applied to a surface, it is not distributed in the material, and, for example, when the material is an absorbing foam, it is not absorbed into the foam, but remains on the surface.

The present inventors have found that by dissolving the active agent, such as e.g. thrombin, in an aqueous solution comprising at least water and ethanol, a more stable jet from the spray nozzle is obtained. Accordingly, in one embodiment of the present invention, the active agent is dissolved in an aqueous alcohol solution, i.e. comprising at least water and one or more alcohols, preferably the alcohols may be selected from methanol, ethanol, propanol, and isopropanol, more preferably an aqueous ethanol solution, i.e. comprising at least water and ethanol. Alternatively, or in addition to the one or more alcohol, the aqueous solution may comprise water and acetone.

Depending on the nature of the active agent, the amount of alcohol present in the aqueous solution may be varied. The amount of alcohol in the aqueous solution may preferably be in a range from 0.01 to 40% v/v, such as e.g. from 0.10 to 40% v/v, from 1 to 40% v/v, from 5 to 35% v/v, from 10 to 30% v/v, from 15 to 30% v/v, more preferably in a range from 15 to 30%, such as e.g. 25% v/v.

The active agent may be any suitable pharmaceutically or biologically active agent, such as e.g. antibacterial, antiseptic, proteins, enzymes, enzyme inhibitors, odour controlling, pain relieving etc or combinations thereof. In one preferred embodiment of the invention, the active agent is selected from the group of enzymes, proteins, peptides and the like; more preferably from the group of enzymes and proteins.

Despite the recent year's advancement in the manufacture of proteins, especially recombinant proteins, such active agents still tend to be expensive. Thus, this method is particularly useful when the active agent is a protein, especially a recombinant protein. In a preferred embodiment of the invention, the active agent is selected from Thrombin, pro-thrombin and active derivatives of Thrombin, or prodrugs of any of these, more preferably Thrombin or pro-thrombin, even more preferably Thrombin. Thrombin or pro-thrombin may be of different grades and activity levels. The method of the present invention may be used for applying any of these different grades.

The present method has proven that the enzymatic activity is maintained during the manufacturing process. Thus, the unnecessary breakdown of active agent often seen due to harsh chemical and physical conditions is avoided. Therefore, the present invention is especially suited where the active agent is an enzymatically active agent, especially Thrombin such as recombinant human thrombin.

It has surprisingly been found, that despite the fact that proteins are well known to be susceptible to denaturation when influenced by alcohols, the method of the present invention when applied to a protein like thrombin, and utilising an aqueous alcohol solution, does not influence the enzymatic activity to any significant degree. As the Examples included herein demonstrate, a protein, here exemplified by thrombin, can be released from the absorbent element of the wound care device. Not only is it released, but the thrombin activity is maintained, as measured by correlation to a thrombin standard dissolved in water (see Example 5).

Not only does the fact that the enzymatic activity is maintained show that our process does not harm the protein, it also shows that our process deposits the active agent on the surface of the absorbent element such that it is all released on contact to saline. Example 3 shows that all of the deposited active agent is released during a 1 minute extraction with PBS. Thus, in contrast to many transdermal patches where a sustained release over hours or days is obtained, this patch provides for an immediate release. This is especially important when the wound care device is to be used in the treatment of bleeding wounds.

In one preferred embodiment of the present invention, the active agent is a protein in an aqueous alcohol solution; more preferably an aqueous ethanol solution; even more preferably an aqueous ethanol solution having an ethanol content in a range from 5 to 35% v/v.

In a specific embodiment of the present invention, the active agent is Thrombin in an aqueous ethanol solution having an ethanol content in a range from 5 to 35% v/v, more specifically from 10 to 30% v/v, even more specifically from 15 to 30% v/v.

When an active agent in an aqueous solution or aqueous alcohol solution is applied to the absorbent element, the desired concentration of active agent on the surface of the final wound care device may be obtained by varying different parameters. Especially the concentration of the active agent, the pump flow, and the speed with which the wound contacting surface of the absorbent element is moved between the spray nozzle and the neutral unit may be adjusted. For example, a high concentration of active agent may require a lower pump flow and/or a higher speed than a less concentrated solution of active agent in order to obtain the same concentration of active agent on the absorbent element. This may for example be measured as $mg/cm^2$, $\mu g/cm^2$ or $U/cm^2$, depending on the specific active agent applied.

In general, the method of the invention may be used to apply concentrated solutions of active agents, for example, the method is well suited to apply a 5% w/v solution Albumin (Albumin used as a test compound, see Example 2 herein). It is envisaged that the method of the present invention may be used to apply from $1 U/cm^2$ to $1000 U/cm^2$ Thrombin. Below, further details are provided with regard to the desirable amounts of Thrombin for treating bleeding wounds, and hence the preferred amounts applied with the method of the invention.

The absorbent element may be prepared from any absorbent material being suitable for use in a wound care device. Preferably the absorbent element is selected from the group of foam, alginates, polysaccharides, chitosans, super absorbent materials or combinations thereof. Additionally, or alternatively, the absorbent element may be prepared from ethylene vinyl acetate (EVA), caprolacton, mPEG-PLGA (PLGA=poly(lactic-co-glycolic acid) or co-polymers of these. It is preferred that the absorbent element is a hydrophilic absorbent element, such as the foam obtained when using a polyurethane foam. Examples 2 and 4 herein show how the electrospray method efficiently provides a polyurethane foam with a thin active layer on the surface of the foam.

Figure 5:
FIG. 5: Cross-section of Bovine Serum Albumin (BSA) electrosprayed onto Biatain®. The foam is ~3.4 mm thick, and the protein is deposited in a thin layer on top of the foam.
Figure 6:
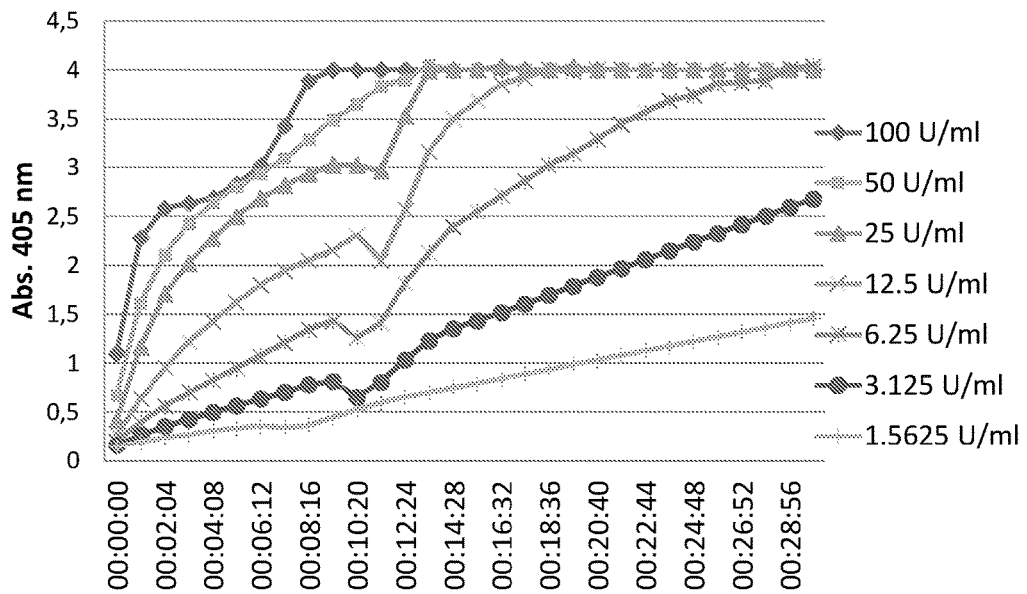
FIG. 6: Activity of Thrombin standards with different concentrations (U/ml), measured as Absorbance every minute for 30 minutes at 37° C.

The thickness of the absorbent element may be as desired for the specific purpose, for example, varying from 0.5 mm to 20 mm, such as e.g. 1 mm to 10 mm, or 1.5 mm to 6 mm. As can be seen from the examples provided herein, the method of the invention provides the absorbent element with a thin layer on the surface without penetrating into the foam (see Example 2, FIG. 5). Additionally, the active agent may easily be released again, further confirming the presence on the surface (see Examples 3 and 5). The thickness of the absorbent element may therefore be selected from criteria other than release of active agent, such as e.g. how much wound exudate is present and/or how much blood is surrounding the wound site. The absorbent element may preferably be of a thickness of 0.5 mm to 6 mm, more preferably 0.75 mm to 5 mm, even more preferably 1.5 mm to 4.5 mm.

A second aspect of the invention relates to a wound care device obtainable by the method described in the first aspect of the invention, including the different embodiments and preferred features mentioned herein.

A third aspect of the invention relates to a wound care device with thrombin on a wound contacting surface of a polyurethane foam.

The wound care device may further comprise a backing layer. The backing layer may preferably be water impervious but vapour permeable. Further details of the wound care device are as described for the first aspect of the invention.

A fourth aspect of the invention relates to a method of stopping bleeding in a human comprising the step of applying to a bleeding wound a wound care device comprising an absorbent element having on a wound contacting surface a layer of thrombin. Further features of the wound care device may be as described herein for the first aspect of the invention. The absorbent element may preferably be a polyurethane foam. The wound care device may preferably be obtained by the method of the invention.

The wound may be any bleeding wound, for example, an exterior wound on the skin surface or an interior wound during surgery.

As Example 3 shows, the thrombin deposited on the wound dressing surface is released immediately. Thus, bleeding will stop within minutes after application of the dressing according to the invention. Example 6 herein shows how a wound care device according to the invention will stop bleeding after an incision in spleen and liver, respectively. As the dressing further has an absorbing element, blood will be absorbed into the absorbing element.

The stopping of bleeding can be even further accelerated by applying compression to the dressing after it has been applied to the wound. As the foams (preferably polyurethane foam) used for wound dressings in general are soft, such compression will not harm the wound or provide the wounded with even more pain. Accordingly, the method of the fourth aspect of the invention may further comprise a step of applying compression to the wound care device. Compression may for instance be applied for 15 seconds to 5 minutes, such as e.g. 30 seconds, 45 seconds, 1 minute, 2 minutes, 3 minutes, 4 minutes or 5 minutes. In many instances, it will be appropriate to apply pressure for 15 seconds to 2 minutes. Example 6 herein exemplifies the use of compression and shows how compression for 1 minute is sufficient to stop bleeding within the first minute of compression (t=0).

In one embodiment of the present invention, the wound care device according to the first, second, third or fourth aspect of the invention has on its wound contacting surface an amount of thrombin in a range from 1 to 200 $U/cm^2$, such as e.g. 1 to 150 $U/cm^2$, 5 to 150 $U/cm^2$, 10 to 125 $U/cm^2$, 15 to 100 $U/cm^2$, or 15 to 90 $U/cm^2$. The herein used unit "U" is an NIH activity unit, and the amount of thrombin is hence indicated by its activity. The amount of thrombin on the wound care device may be varied depending on the intended use of the product, the more severe bleeding, the higher a concentration of thrombin is desired. Suitably, the amount of thrombin is in a range from 10 to 125 $U/cm^2$, preferably in a range from 15 to 100 $U/cm^2$, and even more preferably in a range from 20 to 90 $U/cm^2$. It is envisaged that an amount of 75 $U/cm^2$ may be suitable in a device for stopping severe bleedings. Example 6 herein shows how a device with about 30 $U/cm^2$ will stop bleedings from a small incision in an organ.

Several conventions for activity units are used in thrombin literature and conversion from one convention to another may be needed: 1 IOWA unit=0.83 NIH unit; 1 WHO unit=0.56 NIH unit; 1 NIH unit=0.324+/−0.073 µg; and 1 NIH unit=1 USP unit.

EXAMPLES

Example 1: Application of an Aqueous Solution of Dye on 2 mm Biatain Foam

A model for application of high value active substances.
Summary
A method is developed where an aqueous solution containing an active agent can be applied to a hydrophilic surface with good accuracy and very little loss of material. The solution is pumped by a syringe pump and is electrosprayed onto the foam using an XYZ-robot.

The method is here exemplified using methylene blue on a Biatain® foam (polyurethane foam).
Methods & Materials
  0.5% (w/v) methylene blue (aq)
  Fisnar I&J 9000 robot and controller
  NE-300 syringe pump (New Era Pump System)
  POM mounting bracket and 250×250×3 mm alu receiver (made by Pilot)
  Spray nozzle
  High voltage power supply (Ultravolt)

Experimental

Figure 2:
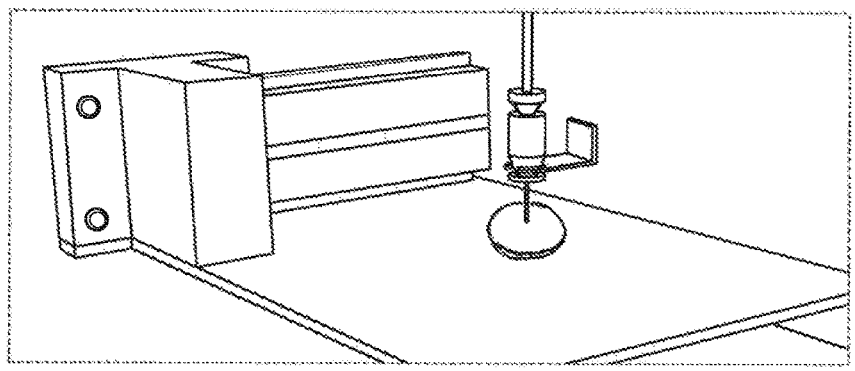
FIG. 2: Close-up of electrospraying setup with stationary spray nozzle and collector plate being bolted to robot arm, as used in Example 1.
Figure 3:
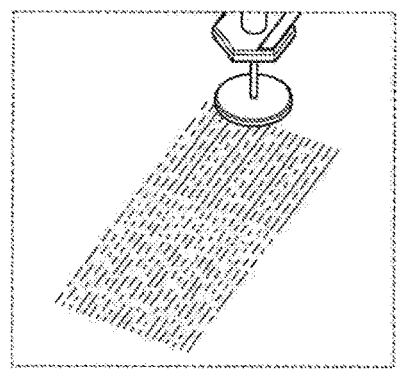
FIG. 3: The electrospraying setup from FIG. 1, with dye sprayed onto the collector plate (dye used for visual purposes).
Figure 4:
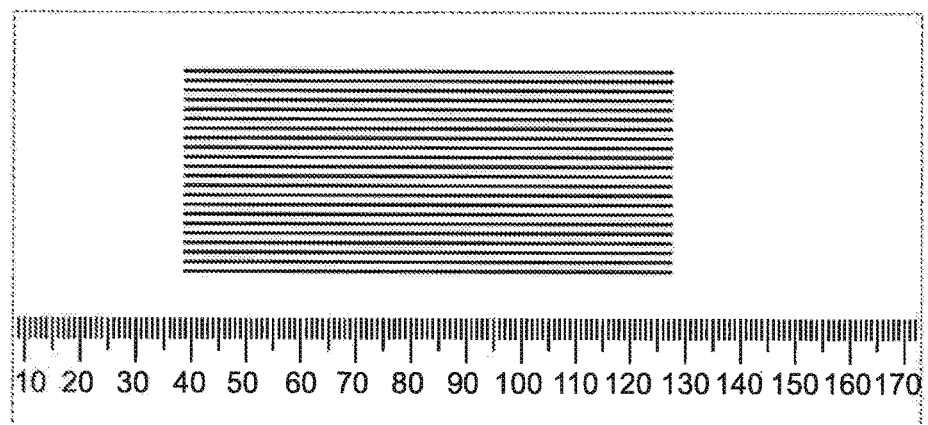
FIG. 4: Dye on Biatain® foam (polyurethane foam).

The robot is programmed to execute the spray pattern as in FIG. 1. Robot is set at origin, voltage is applied and the syringe pump is started. When the spray is stable, the program is started. The Robot setup can be seen in FIG. 2, and the result with dye on collector plate in FIG. 3.
The following parameters were used:
  Distance nozzle/collector: 2 cm
  Voltage collector: 0 kV (ground)
  Voltage nozzle: 10 kV
Pure water was somewhat difficult to spray, probably because of the surface tension, so a 25% (v/v) solution of ethanol was used instead. With this solution, it was possible to get a stable jet of small drops.
  Velocity: 10%
  Flow: 6 ml/h
  Distance (one pass): 3870 mm
  Time (one pass): 3 m 7.24 s
  Volume (one pass): 312 µL
An experiment on Biatain® gave a sharp deposition of the dye on the foam. The foam was then dried for 15 minutes in a vacuum dessicator. The result with dye on the Biatain® foam can be seen on FIG. 4.
Results & Discussion
  Electrospraying: Initial experiments had the nozzle mounted on the robot, but it was soon evident that the electrospraying process is sensitive to vibrations. When the robot was stationary, a stable jet could be formed, but as soon as the robot was started, the spray nozzle started to sputter. The setup was changed so the spray nozzle was stationary and the collector plate was bolted to the robot, i.e. the collector plate is moved under the spray nozzle in order to form the spray pattern. It was then possible to get a stable jet and and fairly sharp and even deposition of dye.
Conclusion
With electrospraying, it is possible to deposit an aqueous solution with accuracy on Biatain® foam. This can be used for application of high value actives.

Example 2: Manufacture of Biatain Patches with Thrombin (75 $U/cm^2$)

Summary
Thrombin is electrosprayed onto Biatain® foam as described in Example 1. Because of the low activity of the thrombin used (68 U/mg), a lot of liquid has to be sprayed onto the foam. This gives rise to some distortion of the product when dried.
Methods & Materials
Thrombin, Calbiochem cat#605157, lot# D00106223, activity 68 U/mg, 1 kU/vial, 30 vials (U=NIH units). Thrombin is dissolved to 10 ml with water and transferred to 10 mL plastic syringe.
Biatain® 3.4 mm, 50×100 mm

Experimental

The robot is programmed to execute the desired pattern. Biatain® is placed at pre-marked location on the collector, robot is made ready, the syringe pump is started and voltage is applied. When the spray is stable, the program is started.

Distance nozzle/collector: 20 mm
Voltage collector: 0 kV (ground)
Voltage nozzle: −13.47 kV
Pump flow 6.15 ml/h
Spraying time/product (12 min 10 sec)

Results & discussion
Electrospraying

Initial experiments was done with a 5% w/v solution of bovine serum albumin (aq) to confirm that it is possible to spray a strong solution of protein. A cross-section of this experiment can be seen in FIG. 5.

This initial experiment showed that:
1. It is possible to spray a 5% w/v solution of a protein
2. The protein is deposited in a thin layer on top of the foam, as opposed to being embedded in the foam.
3. Because the amount of water needed to deposit the BSA is quite high (1.2 mL) the products tend to warp when dried.

This warping can be avoided by spraying a lower amount of water.

The experiment was repeated with thrombin which was sprayed onto the foam with the parameters described above, dried in a vacuum for 4 h and packaged in metalized film with a desiccant (1 g molecular sieve).

Conclusion

Thrombin was deposited as a thin layer onto the patches of Biatain® 50×100 mm with an activity of 75 U/cm$^2$.

Example 3: Measurement of Thrombin in Biatain

Purpose

The purpose of this experiment was to measure if thrombin added to the surface of Biatain® was released again and whether it maintained its activity. The activity of thrombin was used as a measurement of the amount.

Materials and Methods

A 96 wells plate was coated with 0.1% PEG 20.000 at room temperature for 3 hours after which the plate was dried at 37° C.

Assaybuffer: 50 mM Tris-HCl pH 7.4, 150 mM NaCl, 0.1% PEG. Chromozyme stocksolution: (Sigma T1637) 1.51 mM pH til 4.0 diluted to 500 μM in assay buffer.

Thrombin, bovin, plasminogen free (Calbiochem CAL605160) was diluted to the following concentration 100, 50, 25, 12.5, 6.25, 3.125 and 1.5625 U/ml (U=NIH units).

Two pieces of Biatain® (1 cm$^2$) with 200 U thrombin and one piece of Biatain® without thrombin were extracted in phosphate buffered saline (PBS) for 1 min. Each extract should contain 200 U/ml and was diluted to the same concentrations as the thrombin standards.

The assay was performed in the coated 96 well plate by adding the thrombin- or Biatain® dilutions to the chromozyme solution. The enzyme activity was followed by measuring the reaction at 405 nm every minute for 30 minutes at 37° C. with shaking before every measurement.

Results

Figure 7:
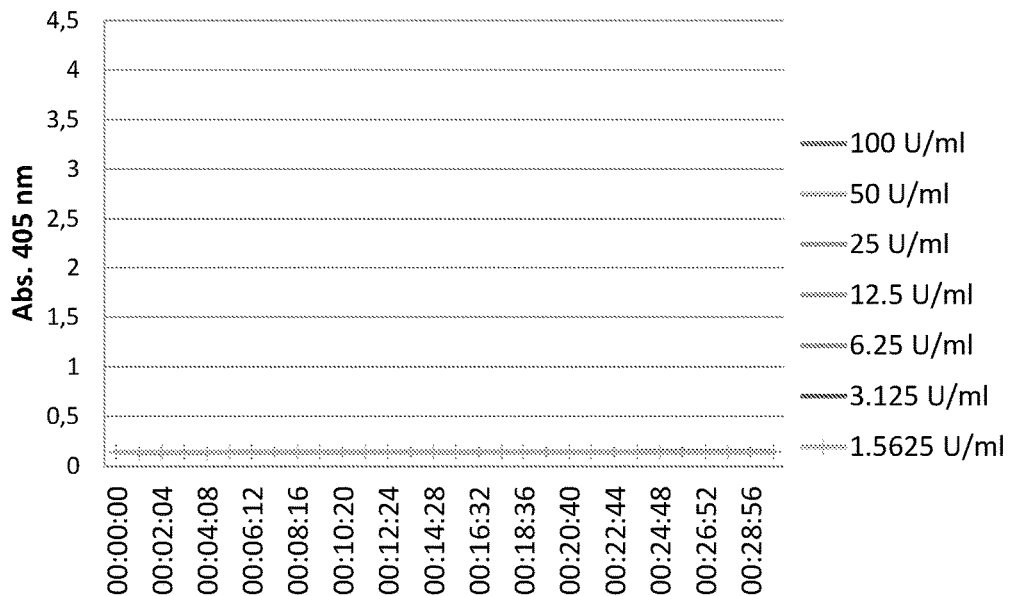
FIG. 7: Activity of extract from Biatain® foam without Thrombin.
Figure 8:
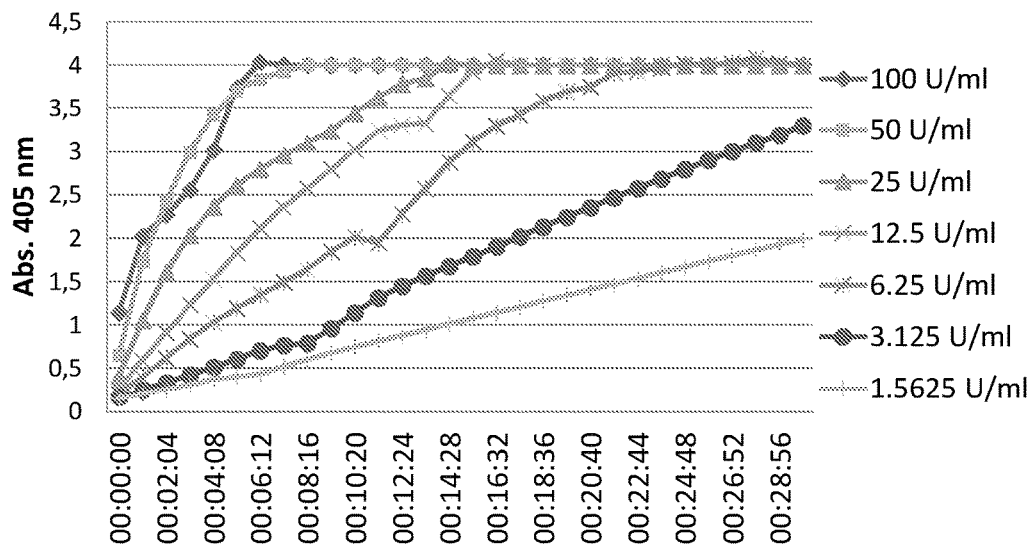
FIGS. 8 and 9: Activity of two extracts from Biatain® foam with Thrombin (sample 1, FIG. 8, sample 2, FIG. 9).
Figure 9:
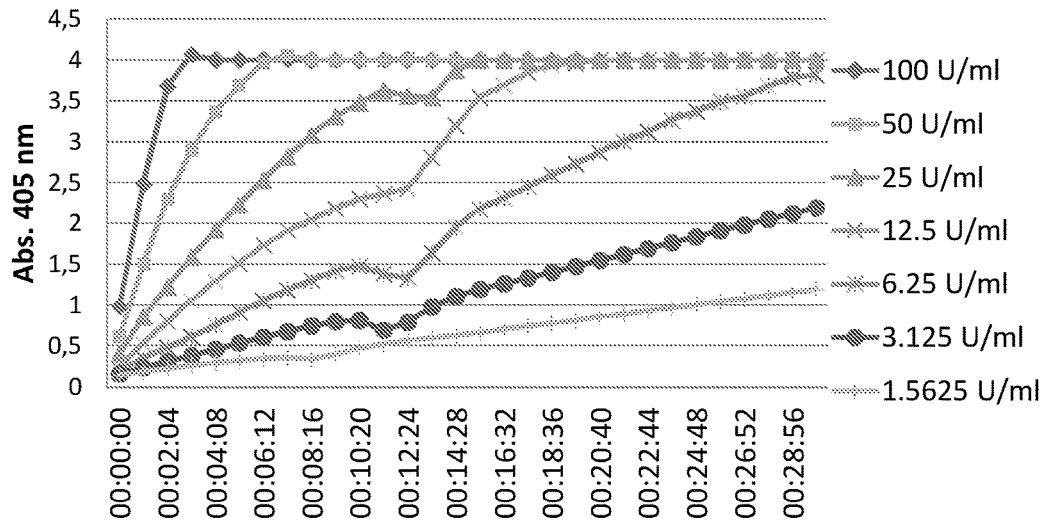
Figure 10:
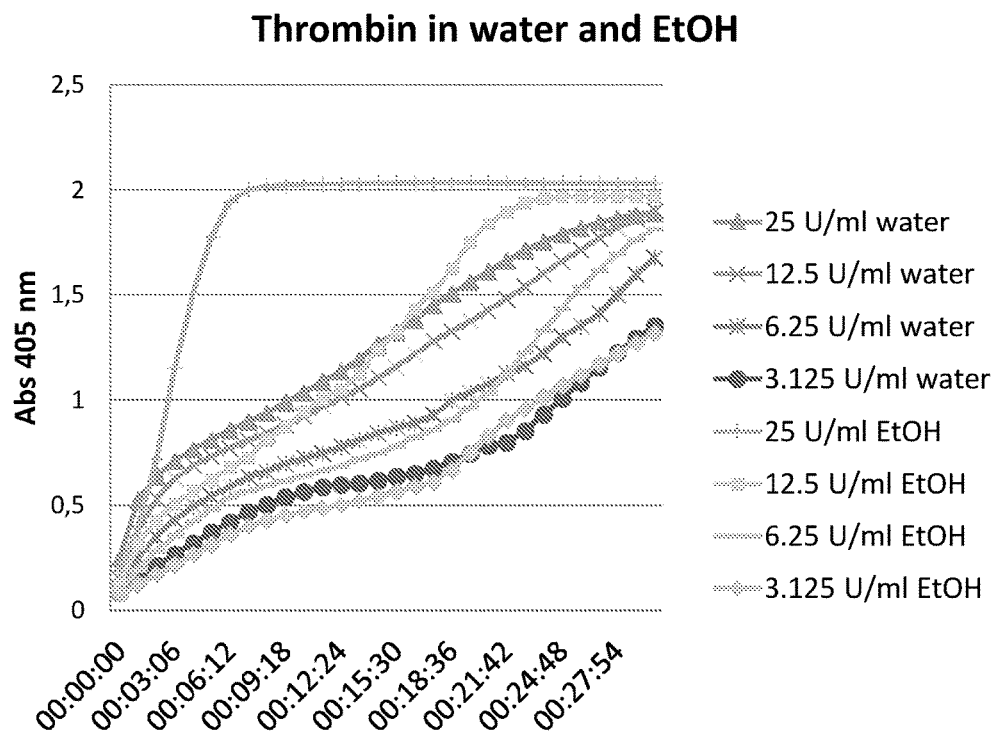
FIG. 10: Activity of Thrombin extracts from Biatain® foam where the Thrombin was electrosprayed dissolved in 25% v/v EtOH or in water.

As shown in FIGS. 6-9, the two samples of Biatain® (Biatain sample 1 (FIG. 8) and sample 2 (FIG. 9)) with thrombin had almost the same curves, and hence the same activity, as the thrombin standard meaning that the Biatain® released all the added thrombin. This also means that the process of adding the thrombin to the Biatain® did not influence the activity of the thrombin. The extract of Biatain® without thrombin did not have any effect on the assay (FIG. 7).

Conclusion

Thrombin added to the surface of Biatain® can be extracted with PBS. The activity of the extract was in the same range as what was added to the Biatain® meaning has the process of adding thrombin to Biatain® had no decreasing effect on the activity.

Example 4: Manufacture of Biatain Patches with Thrombin (27 U/cm2)

Summary

Thrombin is electrosprayed onto Biatain® foam as described in example 2, but at a lower concentration, and with ethanol in the solution Methods & Materials Thrombin, Calbiochem cat#605157, lot# D00106223, activity 68 U/mg, 1 kU/vial, 2 vials (U=NIH units). Thrombin is dissolved to 5.0 ml with 25% (v/v) EtOH(aq) and transferred to 10 mL plastic syringe.

The solution is sprayed onto sheets 2 mm thick Biatain®, and the dots with thrombin are cut from the sheet after drying (1.6×1.6 cm).

Experimental

The robot is programmed to cover an area of 1.6×1.6 cm. The syringe pump is started and voltage is applied and when the spray is stable, the program is started.

Distance nozzle/collector: 12 mm
Voltage collector: 0 kV (ground)
Voltage nozzle: −10 kV
Pump flow 5.25 ml/h
Spraying time 120 s/(1.6×1.6 cm$^2$)

This experiment gives rise to less sputtering and a more stable electrospraying jet than Experiment 2. The product is dried in vacuum, and packaged in foil bags with 2 g of molecular sieve desiccant in an atmosphere of nitrogen.

Example 5: Measurement of Thrombin in Biatain

Purpose

The purpose of this experiment was to measure if thrombin dissolved in 25% EtOH an electrosprayed on Biatain® had the same activity as when thrombin was dissolved in water.

Materials and Methods

A 96 wells plate was coated with 0.1% PEG 20.000 at room temperature for 3 hours after which the plate was dried at 37° C. Assay buffer: 50 mM Tris-HCl pH 7.4, 150 mM NaCl, 0.1% PEG. Chromozyme stock solution: (Sigma T1637) 1.51 mM pH til 4.0 diluted to 500 μM in assay buffer.

Thrombin, bovine, plasminogen free (Calbiochem CAL605160) was diluted to the following concentration 25, 12.5, 6.25 and 3.125 U/ml in EtOH (U=NIH units) and compared with Thrombin from HTI (Haematologic Technologies Inc.) dissolved in water diluted to the same concentrations. The Thrombin from HTI was the only thrombin we had that was dissolved in water but it was an old dilution which might have lost some activities.

Two pieces of Biatain® (1 cm²) with 10 U thrombin applied by electrospraying according to the invention were extracted in phosphate buffered saline (PBS) for 1 min. Each extract should contain 10 U/ml.

The assay was performed in the coated 96 well plate by adding the thrombin- or extract from Biatain® dilutions to the chromozyme solution. The enzyme activity was followed by measuring the reaction at 405 nm every minute for 30 minutes at 37° C. with shaking before every measurement.

Results

The thrombin dissolved in EtOH and in water had the same curves in the different dilutions except in the 25 U/ml where the EtOH had a stepper curves indicating a higher activity. All other dilutions were the same in water and EtOH which indicates that a dilution error might have occurred. This means that thrombin can be diluted in EtOH.

Conclusion

Thrombin dissolved in EtOH and applied to Biatain® by electrospraying had the same activity as when dissolved in water.

Example 6: Haemostasis Using Biatain with Thrombin on Wounds

The Biatain® patches prepared in Example 4, containing electrosprayed thrombin ~30 U/cm² (27 U/cm²), were used in an experiment to stop bleeding in spleen and liver on pigs.

Figure 11:
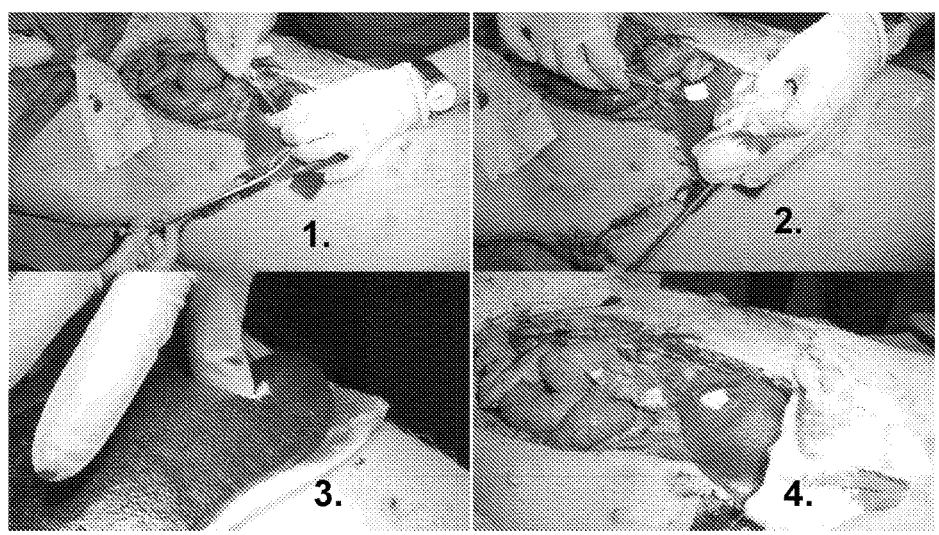
FIG. 11: Study procedure for haemostatis experiment using Biatain® on wounds.

The study procedure can be seen in FIG. 11, and consist of the following steps:
1) make a wound by incision in spleen (A: 0.8×0.8 cm and B: 1×1 cm) or liver (C: 1×1 cm);
2) apply the ~2×2 cm² Biatain® patch (1.6×1.6 cm²);
3) apply compression for 1 min;
4) look for haemostatis immediately (t=0) and after 1 and 5 min.

A comparison is made with a control: an identical Biatain® patch without any thrombin.

Figure 12:
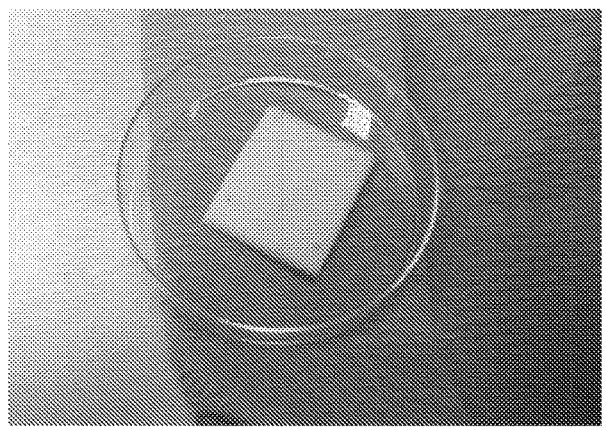
FIG. 12: Biatain® patch prior to application.
Figure 13:
FIGS. 13-15: Results from haemostatis experiment in spleen (A: 0.8×0.8 cm incision; B: 1×1 cm incision) and liver (C: 1×1 cm incision).
Figure 14:
Figure 15:
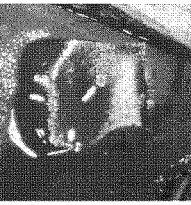
Figure 15:
Figure 15:
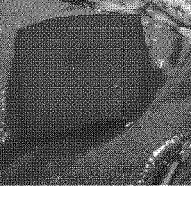
Figure 15:
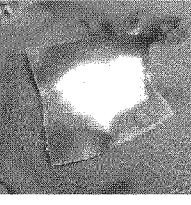
Figure 15:
Figure 15:

The Biatain® patch prior to being applied can be seen in FIG. 12. Experiment A and B with spleen can be seen in FIGS. 13 and 14, respectively. Experiment C with liver can be seen in FIG. 15.

CONCLUSION

It can be seen from FIGS. 12-15 that the control patches have no haemostatic effect, and are pushed away from the wound by the blood, i.e. there is continued bleeding beneath the control patches. The patches with Thrombin provide haemostatic effect, at T=0 there is a little bleeding in the center of the patch, which does not increase as compared to the control. The blood seen at the edges of the Thrombin patches are due to the surroundings. In conclusion, the electrosprayed Thrombin patches provide good haemostatic effect.

The invention claimed is:

1. A method of preparing an absorbent wound care device comprising the steps of:
   a) providing a wound care device comprising a polyurethane foam absorbent element, said element having a wound contacting surface and opposite thereof a backing surface;
   b) providing an active agent comprising thrombin dissolved in an aqueous alcohol solution, wherein the alcohol is present in the aqueous solution from 15 to 30 percent v/v;
   c) electrospraying the active agent comprising thrombin dissolved in the aqueous alcohol solution onto the wound contacting surface of the polyurethane foam absorbent element to form a layer of thrombin on only the wound contacting surface without penetration into the polyurethane foam to provide a thrombin coated wound contacting surface treated polyurethane foam; and
   d) drying the treated polyurethane foam, wherein the thrombin is immediately released from the coated layer of thrombin deposited onto the wound contacting surface under physiological conditions.

2. The method according to claim 1, wherein the electrospraying of step c) comprises:
   providing a stationary charged spray nozzle with the active agent comprising thrombin;
   providing an opposing stationary neutral unit; and
   moving the wound contacting surface of the polyurethane foam absorbent element between the spray nozzle and the neutral unit, wherein the active agent comprising thrombin is deposited onto the wound contacting surface.

3. The method according to claim 2, wherein the stationary charged spray nozzle is negatively charged.

4. The method according to claim 1, wherein the active agent comprising thrombin is recombinant human thrombin, pro-thrombin, prodrugs of thrombin, or prodrugs of pro-thrombin.

5. The method according to claim 1, wherein the aqueous alcohol solution is an aqueous methanol, ethanol, propanol, or isopropanol solution.

6. The method according to claim 5, wherein the aqueous alcohol solution is an aqueous ethanol solution.

* * * * *